United States Patent [19]
Hwang

[11] Patent Number: 5,108,425
[45] Date of Patent: Apr. 28, 1992

[54] LOW TURBULENCE HEART VALVE

[76] Inventor: Ned H. C. Hwang, 2155 Lochlevin Dr., Memphis, Tenn. 38119

[21] Appl. No.: 530,335

[22] Filed: May 30, 1990

[51] Int. Cl.⁵ .............................................. A61F 2/24
[52] U.S. Cl. ............................................... 623/2
[58] Field of Search ...................................... 623/2

[56] References Cited

U.S. PATENT DOCUMENTS

| | | | |
|---|---|---|---|
| 4,011,601 | 3/1977 | Clune et al. | 3/1.5 |
| 4,425,670 | 1/1984 | Figuera | 3/1.5 |
| 4,484,365 | 11/1984 | Murguet et al. | 3/1.5 |
| 4,535,484 | 8/1985 | Marconi | 623/2 |
| 4,775,378 | 10/1988 | Knoch et al. | 623/2 |
| 4,808,180 | 2/1989 | Johnson | 623/2 |
| 4,846,830 | 7/1989 | Knoch et al. | 623/2 |
| 4,872,875 | 10/1989 | Hwang | 623/2 |

Primary Examiner—Randy C. Shay
Attorney, Agent, or Firm—Fitch, Even, Tabin & Flannery

[57] ABSTRACT

A heart valve having a pair of leaflets of identical construction provides low pressure drop and freedom from thrombosis and hemolysis. The leaflets have flat sections wherein a pivot mechanism is incorporated and curved sections which are located downstream of the flat sections. The outflow or facing surface of each of the two leaflets is of two-dimensional, convex curvature whereas the opposite or inflow surface regions are of a composite concave-convex curvature on both sides of a central ridge which bisects the curved inflow surface section of each leaflet. The curvature of the downstream regions of each leaflet is fashioned so that a peripheral surface, which extends about the arcuate downstream edge of each leaflet, is of a substantially constant and relatively minimal thickness. As a result, not only is there extremely low boundary layer separation in the blood flowing along the surfaces of the leaflet but there is extremely low turbulence in the bloodstream just past the trailing edge which minimizes hemolysis at this point.

20 Claims, 3 Drawing Sheets

LOW TURBULENCE HEART VALVE

The present invention relates to heart valve prostheses and more particularly to prosthetic heart valves having one or more pivotal valve members, particularly bileaflet heart valves, which create only very low turbulence in the bloodstream.

BACKGROUND OF THE INVENTION

A wide variety of heart valve prostheses have been developed which operate hemodynamically in unison with the pumping action of the heart. Some of the earliest valves included a ball and cage arrangement, and subsequent valves were developed utilizing a single disc or occluder that either floated, or pivoted along an eccentric axis, between open and closed positions. Subsequently, various streamlined designs were advocated so as to improve the performance of such valves. Examples of valves of this type are shown in U.S. Pat. Nos. 4,011,601, 4,425,670, and 4,484,365. At about the same time, prosthetic heart valves employing a pair of occluders were developed, and these valves are often referred to as bileaflet valves. In such an arrangement, both of the occluders are generally identical in shape and size and are designed to pivot about eccentric axes. U.S. Pat. Nos. 4,535,484 and 4,846,830 are representative of such bileaflet valves. Although the patent art is replete with different designs for prosthetic heart valves, the majority of such designs have never achieved commercial reality, often because particular advantages which the valve may have are accompanied by shortcomings that prevent their commercialization.

In general, a prosthetic valve should provide a relatively unobstructed, fairly wide open passageway when in the open position, so as to only minimally retard the flow of blood therethrough in the downstream direction, creating a relatively low pressure drop across the valve. In addition, the design should be such as to eliminate or minimize turbulence by delaying blood flow separation from the leaflet surfaces. Turbulence created at the valve can result in hemolysis (the rupture of individual blood cells) and thrombosis (the formation of blood clots), and it is now considered very important to avoid turbulence. Moreover, a prosthetic heart valve should be very responsive to the repetitive changes in the direction of blood flow, so as to quickly open during the pumping stroke and quickly close as soon as the heart relaxes the pumping chamber to thus prevent substantial regurgitation of blood. Furthermore, the opening and closing of such a heart valve should be sufficiently soft so as not to disturb the patient with audible sounds, and of course the heart valve should be constructed so as to withstand countless openings and closings.

U.S. Pat. No. 4,872,875, issued Oct. 10, 1989, discloses heart valve designs for both single occluder and bileaflet heart valves. The occluders are designed with a streamlined shape having an upstream generally flat section that leads to downstream section which vary in thickness; these downstream sections have surfaces which are three-dimensional in shape but which are formed with particular two-dimensional curved designs to eliminate boundary layer separation and thereby minimize the drag upon blood flow in the open position. Although such a design has substantial theoretical advantage, it is primarily based upon considerations applicable to surfaces of infinite length; because heart valve occluders are of finite length, edge effects become of considerable importance. Moreover there will no doubt always be areas for improvement in any heart valve design, and accordingly improved heart valve designs continue to be sought.

SUMMARY OF THE INVENTION

The present invention provides improved heart valves having valve members or occluders which are designed to not only provide quick response to opening and closing and a relatively low pressure drop thereacross but also to minimize turbulence in the blood flow pattern which can give rise to hemolysis and/or thrombosis. It was found that the trailing or downstream edge of an occluder in the open position can give rise to significant turbulence in regions just downstream of where the flow exits from the surface of the occluder. By narrowing the curved peripheral surface and appropriately attenuating the concave-convex curvature of the inflow or upstream surface so that it smoothly terminates at such a peripheral surface of substantially constant height, it has been found that turbulence is substantially eliminated across the entire width of the leaflet.

DETAILED DESCRIPTION OF THE PREFERRED EMBODIMENTS

FIGS. 1-11 show a preferred embodiment of a heart valve prosthesis embodying various features of the present invention. The heart valve 10 is of bileaflet construction, but it will be readily apparent to one of ordinary skill in the art that the principles of the present invention can be applied to a prosthetic heart valve having single occluder to attain similar advantages. Heart valves of this general type exhibit improved flow in the fully open position eliminating boundary layer separation along the major surfaces of a pair of leaflets or a single occluder and turbulence downstream of the trailing edges thereof. This design not only minimizes drag on blood flowing therethrough, but also excellently avoids stagnation which might lead to eventual clotting while at the same time avoiding hemolysis and thrombosis. In addition, heart valves of this design have a rapid response to opening and closing forces and a relatively small impact upon contact between the occluders and the valve body.

Figure 1:
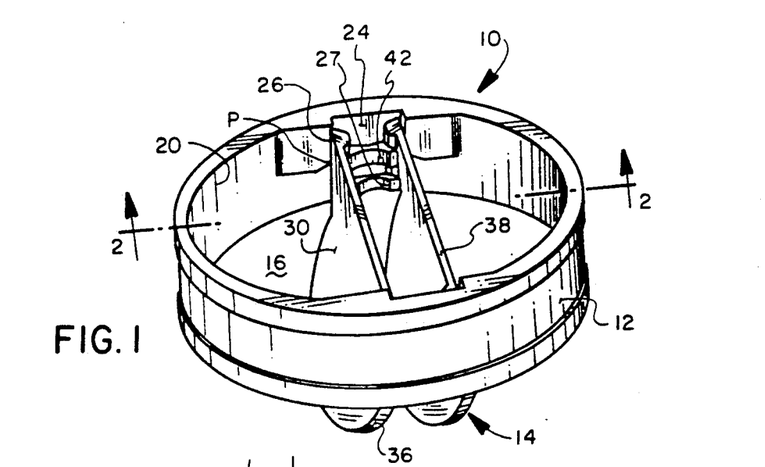
FIG. 1 is a perspective view of a bileaflet heart valve embodying the various features of the present invention, shown in its open position.
Figure 2:
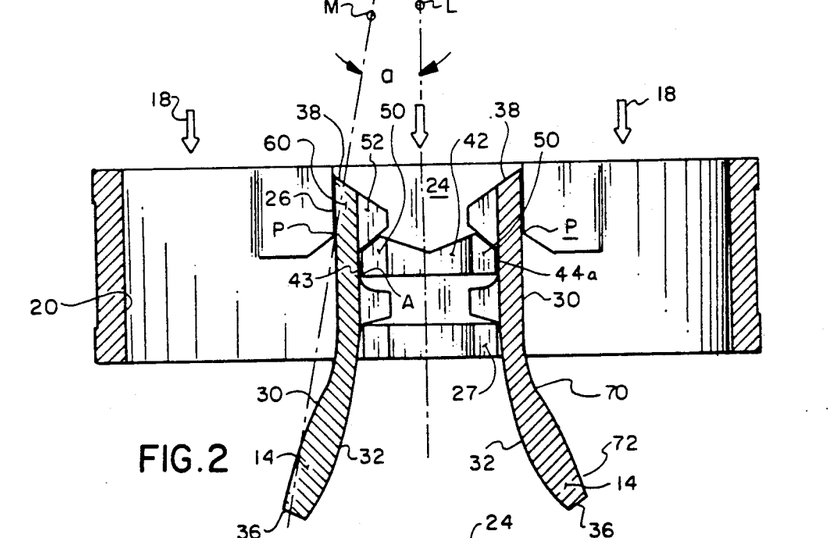
FIG. 2 is an enlarged cross-sectional view of the heart valve taken along line 2—2 of FIG. 1, showing the valve in its open position.

As best seen in FIGS. 1 and 2, heart valve 10 includes a generally annular valve body 12 and a pair of pivoting valve occluders or leaflets 14, which open and close to control the normal flow of blood in the downstream direction of arrows 18 (FIG. 2). Blood flows through an interior passageway 16 which is preferably circular in cross section being defined by a generally cylindrical internal surface or sidewall 20 of the body 12 which is interrupted by a pair of diametrically opposed flat wall sections 24. The exterior surface is formed to facilitate the attachment of a sewing ring or the like, as well known in the art, which allows the valve to be sutured in place in the human heart. Flanking the flat wall sections are a pair of abutments 26 which serve as fulcrums and stops for closing movement and which also act in conjunction with a downstream protrusion or ledge 27 to halt the rotation of the leaflets when the leaflets reach a fully open position, as illustrated in FIGS. 1 and 2.

Diametrically opposed projections 42 extend generally perpendicularly outward from the two flat wall sections 24; each projection 42 has a pair of oppositely facing lateral pivots 43. Each pivot is made up of three flat seating surfaces or facets 44a, 44b and 44c, and each facet is oriented at between about 110° and about 130°, and preferably approximately 125°, from the next adjacent facet. In the preferred embodiment, the facet 44a is oriented generally parallel to the axis of blood flow, with the facets 44b and 44c lying respectively upstream thereof. The center section of each projection 42 is recessed so as to minimize the transverse surface area in the path of the flow of blood through the passageway 16. The inward facing end surfaces 50 of the projections 42 are flat and generally parallel to the flat wall section 24 of the valve body. Thus, the three facets 44a, 44b, and 44c are preferably each perpendicular to these end surfaces 50. As discussed below, these pivots 43 matingly engage notches 53 formed in the leaflets 14.

Each leaflet 14 has an upstream or inflow surface 30 and an opposed downstream or outflow surface 32. As best seen in FIG. 2, which is sectioned along the central plane which bisects the leaflet and lies perpendicular to the pivot axis, it is apparent that the cross-sectional thickness of the leaflet varies considerably in the section downstream of the pivot axis. As discussed hereinafter, the specific three-dimensional composite curvature of the leaflets reduces boundary layer separation adjacent the major leaflet surfaces to minimize drag against blood flowing throughout the heart valve and more importantly avoids the creation of turbulence downstream of the trailing edges of the leaflets. The curvature of the downstream section of the leaflets also assures rapid response of the leaflets to reversals in the direction of blood flow. The rapid response time is also attributable to the novel hinge mechanism, the details of which are set forth in copending U.S. Patent application Ser. No. 392,745, filed Aug. 11, 1989, the disclosure of which is incorporated herein by reference.

The inflow surfaces 30 of the leaflets have a flat region 68 which is joined to two regions 70 of concave curvature lying on opposite sides of the central bisecting plane along which an upstanding ridge 80 is formed in the inflow surface. As explained hereinafter, each curved surface region is preferably made up of a series of straight lines which, although not parallel to one another, all lie in parallel planes, preferably planes which are perpendicular to the central plane along which FIG. 2 is taken. Each leaflet inflow surface 30 also includes two convex regions 72 downstream of the concave regions 70. The convex regions 72 may each have a curvature generally resembling a section of a paraboloid, an ellipsoid or some other smoothly curved shape when viewed in cross section in a plane parallel to the central plane. In the embodiment which is illustrated, the junctions between the major leaflet surface regions are blended so as to provide a continuous smooth composite curved surface sloping downward on each side of the central ridge 80 which bisects the curved downstream section of the leaflet inflow surface.

The outflow surfaces 32 of the illustrated leaflets 14 have a flat portion 75 and a single convex surface portion 76 in that region which lies opposite the inflow concave regions 70 and the inflow convex regions 72. Overall, the leaflets have a maximum thickness along the central plane at the location where the convex surfaces 76, 72 oppose one another and a flat section in the upstream region where the pivot is located. The opposed inflow and outflow surfaces terminate along peripheries that define the major arcuate section 36, which preferably has a constant thickness and a curvature that is dictated by its junction with the sidewall 20 of the valve body, against which it lies in juxtaposition upon the valve closing. The convex surface portion 76 lies downstream of the pivot axis which is located in the flat section of the leaflet bounded by the surfaces 68 and 75; this section preferably has a constant thickness that is preferably the same as that of the arcuate surface section 36.

In addition to the arcuate peripheral surface 36, which is located at the trailing or downstream end of each leaflet in the open position, a minor flat surface 38 is located at the opposite, leading end of the leaflet (again, assuming a leaflet in an open position). This minor surface 38 is oblique to the flat section of the leaflet 14, being formed at an obtuse angle to the flat portion 75 such that the two minor surfaces 38 of the pair of leaflets 14 abut or mate in surface-to-surface contact along substantially their entire lengths when the valve is in the closed position.

The peripheral surface of each leaflet 14 also includes a pair of opposed, short lateral surfaces 51 which are interposed between the major arcuate surface section 36 and the minor mating section 38. These lateral surfaces 51 of the leaflets are preferably flat, and the leaflets are proportioned so as to provide a minimal clearance 25 (FIG. 3) with the flat wall sections 24 of the valve body 12, beside which the leaflets 14 pivot.

A pair of extensions 52 extend from the outflow surface 32 of each leaflet 14 in the regions of the flat lateral surfaces 51. The pair of extensions 52 have lateral surfaces that are generally perpendicular to the flat sections of the leaflets, and they contain notches 53 that are proportioned to receive the pivot projections 42. An upstream surface 54 of each extension 52 is oriented at the same oblique angle as the mating section 38 of the peripheral surface so as to form a continuous coplaner surface therewith. The downstream end surfaces 59 of the extensions 52 are generally similarly oriented at an oblique angle to provide adequate strength, as well as to function in conjunction with the protrusions 27 which extend inward from the interior surface of the valve body and serve as lower stop surfaces. More particularly, the upper edges 77 (FIG. 4) of the stop surfaces engage the oblique end surfaces 59 of the extensions 52 just before the pivoting leaflets reach their fully open position. As a result, they both cushion the leaflets and slightly lift the leaflets upstream, breaking contact between the notches 53 and the pivots 43 and thus reducing wear along the interengaging surfaces that define the pivot axes.

Figure 3:
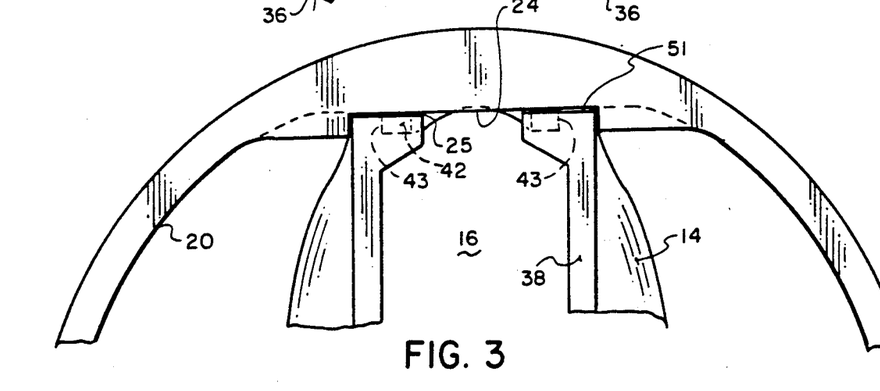
FIG. 3 is a fragmentary plan view of the bileaflet heart valve shown in FIG. 1, with the valve in the open position.
Figure 4:
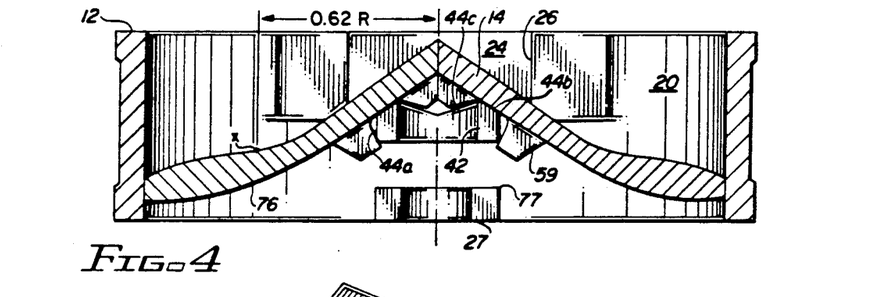
FIG. 4 is a view similar to FIG. 2 with the valve in the closed position.
Figures 5, 6, 7:
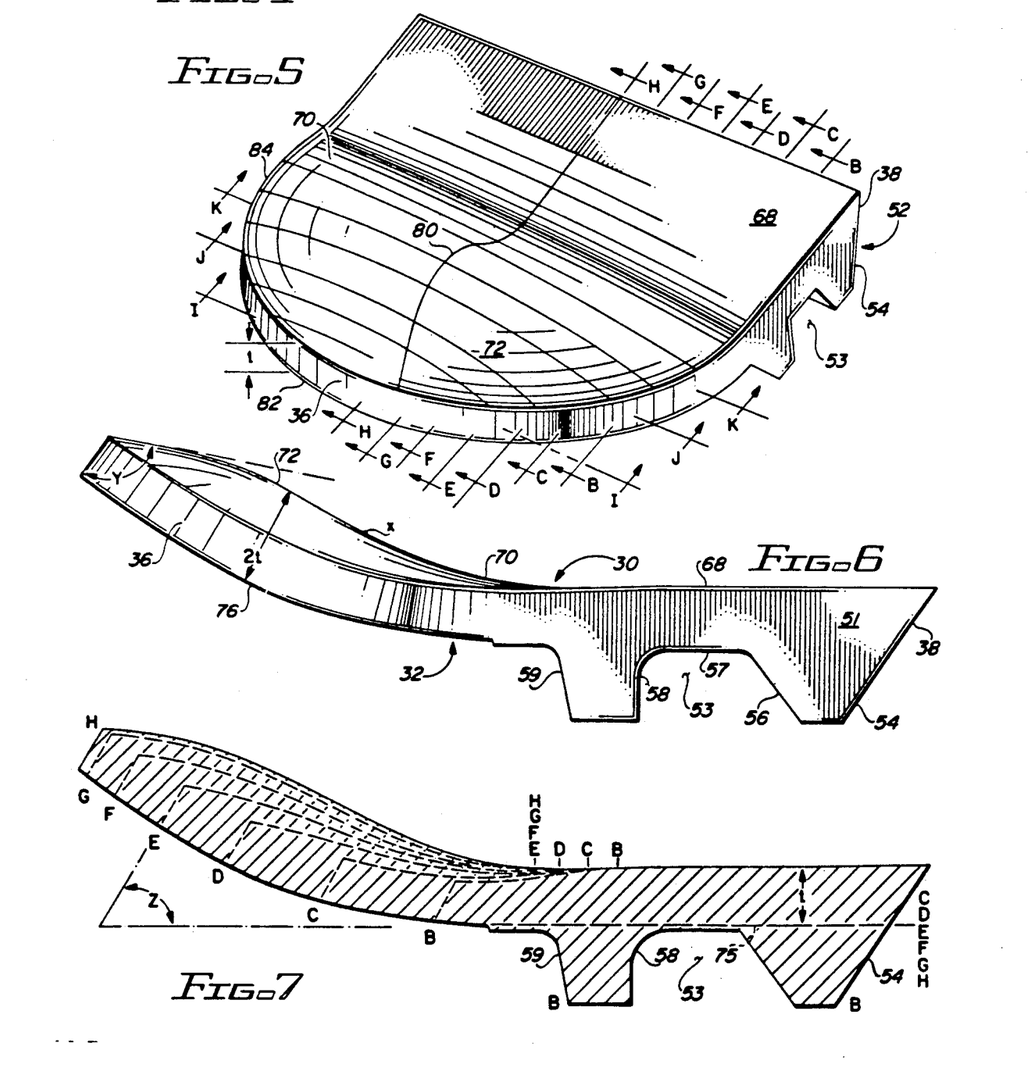
FIG. 5 is a perspective view looking at the inflow or upstream surface of a leaflet from the valve in FIG. 1.
FIG. 6 is a side elevation view of the leaflet shown in FIG. 5.
FIG. 7 is a cross-sectional view taken looking along the lines H—H of FIG. 5 with a series of additional cross-sectional outlines taken along lines B—B through G—G superimposed thereupon in broken lines.

The notches 53 are partly defined by two flat surfaces 56 and 57 oriented so as to lie in juxtaposition with the facets 44a and 44b when the leaflets are in the closed position, as best seen in FIG. 4. The flat surface 57 is parallel to the flat region 75 of the outflow surface. On the downstream side of the flat surface 57, the notch 53 is formed with a curved surface 58 which functions to improve the opening response of the leaflets, as more particularly described in the aforementioned U.S. patent application. As best seen in FIG. 3, the extensions 52 are flat along their laterally outward sides and tapered or oblique along their laterally inward sides; this construction provides good structural strength in the regions of the pivot. Because it is desired that the leaflets 14 be relatively thin so as to provide as clear a passageway as possible for blood flow through the valve in the open position, the extensions are designed to assist in withstanding the stresses of pivoting and to reinforce the leaflets in these regions. The leaflets are preferably manufactured or fabricated so that the extensions are integral with the remainder of the leaflet. As best seen in FIGS. 6 and 7, to carry out this reinforcement function, the flat surfaces 57 of the extensions are located so as to be spaced slightly below the plane of the flat portion 75 of the outflow surface, thereby providing additional thickness in this region where the stress will be greatest.

As best seen in FIGS. 5 though 7, the arcuate section 36 of the peripheral surface is preferably of constant thickness, and this thickness is represented by the reference (t). Most preferably, the thickness is substantially the same as the thickness of the flat section of the leaflet which is indicated in FIG. 7 as also having a thickness t; however, there could be some difference between the relative thicknesses if desired. For leaflets of this configuration, where the inflow surface region is bisected by a central ridge from which the streamline compound-curved inflow surface regions slope downward, it has been found that the maintenance of such a constant thickness for the peripheral surface results in extremely low turbulence downstream of the trailing edge of the leaflets when blood is flowing in the fully open position.

In the embodiment of the leaflets depicted in FIGS. 5 through 11, the convex portion of the outflow surface 32 is a smooth two-dimensional surface; however, it might also be bulged slightly or have a slight three-dimensional curvature. The corresponding region of the inflow surface 30 is of complex three-dimensional curvature, and as best seen in FIG. 5, the leaflet is thickest along its central plane where the raised central ridge 80 is located. At the highest point on the ridge, the thickness is equal to about 2t (see FIG. 6). FIGS. 5 through 7 best show the overall compound curvature of the inflow surface 30, which has a convex region 72 formed downstream from the concave region 70. The concave region 70 is preferably tangent to the flat region 68. The concave region 70 and the convex region 72 are also preferably tangent to each other at the junction therebetween and of about equal length when measured in the central plane, and the point of the tangency along the central plane is shown in FIG. 6 by the reference "X". Performance of the leaflets is improved by the proper location of this point of the tangency between the convex and concave surface regions in the inflow surface of composite curvature. More particularly, the convex and concave surfaces regions should be located so that, when the leaflets are positioned in a valve body of a circular cross section having a radius of "R", and when the two leaflets are disposed in their blocking position as shown in FIG. 4, the point of tangency in the central plane is located at a distance from the centerline of the valve body between about 0.6 R and about 0.7 R. As depicted on FIG. 4, in the illustrated embodiment, the point X is located at a distance of about 0.62 R from the centerline of the valve body.

In addition, the convex surface region 72 of the inflow surface preferably has a radius of curvature, measured in the central plane (see, for example, side elevation view FIG. 6) between about 0.5 R and about 0.7 R, and the concave surface region 70 preferably also has a radius of curvature, measured in the central plane, between about 0.5 R and about 0.7 R. The radius of the curvature of the convex portion 76 of the outflow surface 32 is larger, and it is preferably between about 0.9 R and 1.1 R. As can be seen from FIG. 5 and as is also clear from FIGS. 8-10, the composite curved regions of the inflow surface slope downward in both lateral directions from the central ridge 80. In other words, each leaflet, when bisected by a central plane or midplane perpendicular to the pivot axis of the leaflet, is divided into two halves which are mirror images of each other. In actual practice, the ridge 80 is not a sharp line but is just slightly ground and polished to provide a smooth ridge.

It can be seen from FIG. 5 that each half of the leaflet has an inflow surface which slopes from the central ridge to the arcuate peripheral edge which is of constant height, as explained hereinbefore, preferably having the height or thickness t. As also indicated hereinbefore, the curvature of the arcuate section 36 of the peripheral surface is dictated by the intersection of the leaflet with the interior surface 20 of the valve body so that the arcuate surface of each leaflet lies closely adjacent to and in substantial abutting contact with the sidewall when the leaflets are in the closed or blocking position. It can be seen from FIG. 4 that, in essence, the lower edge 82 of the peripheral arcuate surface section 36 is determined by the radius of curvature of the convex portion 76 of the outflow surface. Inasmuch as the arcuate section 36 is of constant height, the location of the upper edge 84 of the peripheral surface is in turn defined by the location of the lower edge 82.

Figure 8:
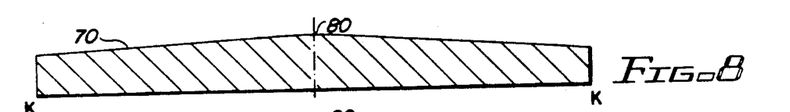
FIGS. 8 to 10 are sectional views taken along the lines K—K, J—J and I—I of FIG. 5.
Figure 9:
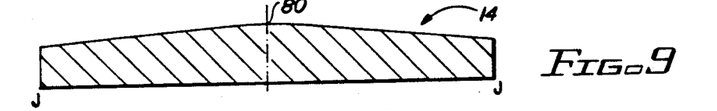
Figure 10:
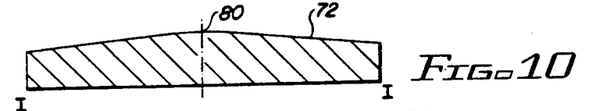

It has been found that the desired streamlining of flow results from fashioning the compound curvature of the downstream section of the inflow surface 30 so that the surface extends from the ridge 80 lying in the center plane to the peripheral edge 84 in the form of a series of straight lines, or of substantially straight lines. In the preferred embodiment, if the inflow surface 30 is cut by a series of parallel planes perpendicular to the center plane that bisects the leaflet and parallel to a reference axis or plane, such planes will each cut the surface along a straight line. In FIGS. 5-11, the set of planes are parallel to the flat mating surface 38 (and at an angle of about 55° to the flat portion 75 of the outflow surface) will result in surfaces 70 and 72 formed by straight lines which appear perpendicular to the central plane when viewed from above. As explained hereinafter, such a set of parallel planes need not be parallel to the mating surface 38 but could be angularly offset therefrom by up to about 40° in either the upstream or downstream direction. These surfaces are thus sometimes referred to as rectilinear surfaces. The cross sectional configurations of the leaflet 14 when cut by three such planes along the reference lines I—I, J—J and K—K of FIG. 5, are depicted in FIGS. 8-10, which illustrate such straight line configuration, sloping laterally in both directions from the center ridge 80. The slope is preferably such that these straight lines form an angle between about 95° and about 110° with the peripheral surface, as best seen in FIGS. 8-10.

Fabrication of the leaflets in this fashion accomplishes the desirable effect that the radii of curvature of the convex and concave surfaces continuously uniformly increase, from a minimum value along the center ridge 80, laterally in either direction toward the arcuate edge 84 of the leaflet. This can be seen in FIG. 7 where a series of cross sectional configurations of the leaflet are shown in dashed lines using the reference numerals B through H which appear on FIG. 5. This constant uniform increase in the radii of curvature in a direction laterally outward from the center plane is found to improve performance because, for the flow of liquid, i.e. blood, through the heart valve 10 with the leaflets 14 in the open position shown in FIGS. 1-3, the flow rate will be greatest along the centerline and will be least near the lateral edges of the leaflets. Accordingly, this change in radii of curvature of the composite curved inflow section is generally matched to the change in velocity of blood flow over the inflow surface, with a resultant increase in overall performance and decreases both in turbulence adjacent the trailing edge (which can cause hemolysis) and in pressure drop across the valve.

In addition to the foregoing factors, it has also been found that turbulence downstream of the trailing edge of the leaflet is minimized when the angle Y between the peripheral surface and a line tangent to the convex surface region 72, when measured in the central plane (see FIG. 6), is between about 110° and about 120°, and preferably between about 114° and about 117°. Thus, when the convex curvature of the outflow surface is maintained within the parameters hereinbefore indicated and the angle Y falls between these limits, the undesirable trailing edge effect is greatly negated, minimizing the turbulence downstream which can give rise to hemolysis.

As explained hereinbefore, the concave and convex surface regions on each side of the central ridge 80 are preferably formed as surfaces that are straight lines, when cut by sets of parallel planes which are perpendicular to the central plane or midplane (along which the center ridge 80 lies). This set of parallel planes should be disposed at an angle "Z" of between about 15 degrees and about 95 degrees to the plane of the flat outflow surface portion 75. For example, the curved surfaces in FIGS. 5-7 are formed by straight lines extending from the center ridge 80 to the arcuate edge 84 in planes which are perpendicular to the midplane and parallel to the flat mating surface 38 (and thus at an angle Z of about 55°, see FIG. 7, to the plane of the flat outflow surface of the leaflets). However it may be preferable to have the set of parallel planes oriented at an angle "Z" between 65 degrees and about 95 degrees.

Figures 11, 12, 13, 14, 15:
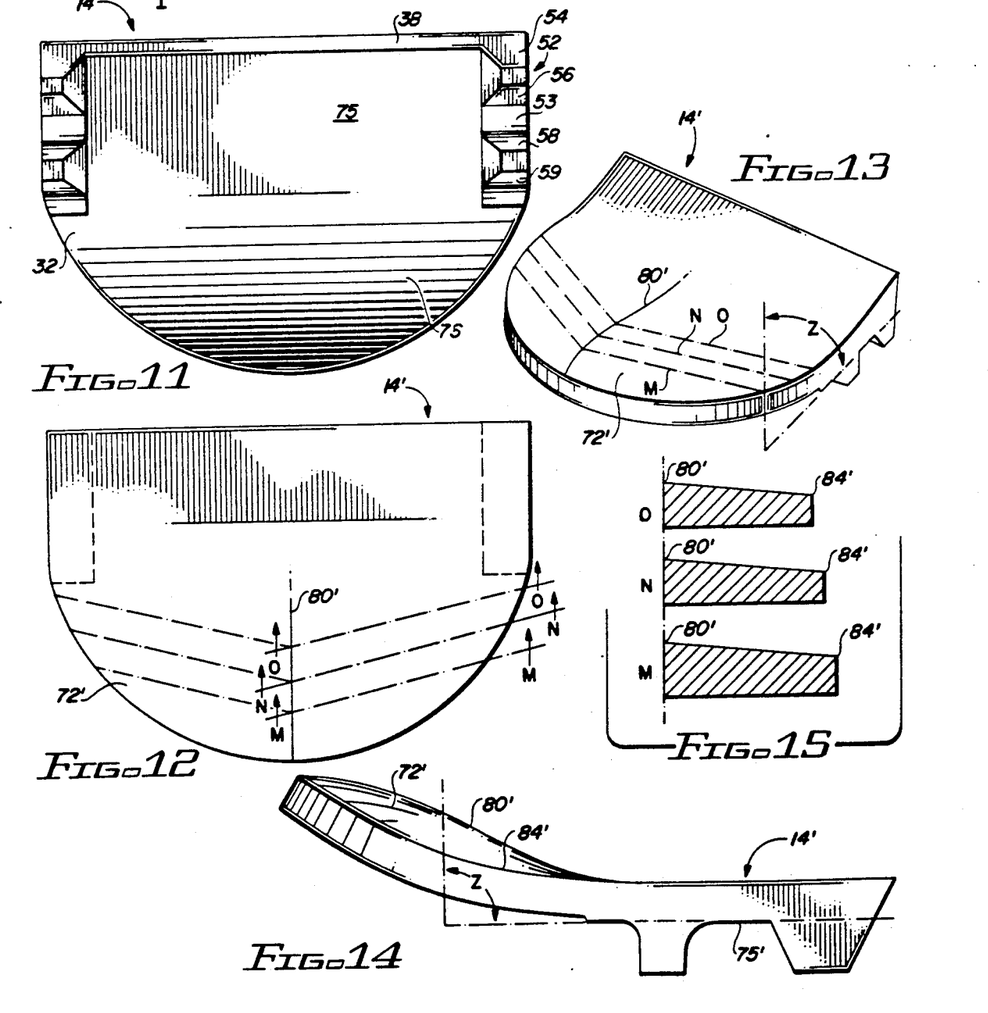
FIG. 11 is a bottom view of the leaflet shown in FIG. 5 looking at the opposite or outflow surface thereof.
FIG. 12 is a top view of an alternative embodiment of a leaflet, generally similar to that illustrated in FIGS. 5 to 11, which also embodies various features of the invention.
FIG. 13 is a perspective view of the leaflet of FIG. 12.
FIG. 14 is a side elevational view of the leaflet of FIG. 12.
FIG. 15 is a group of three fragmentary sectional views taken along the reference lines indicated in FIGS. 12 and 13.

Shown in FIGS. 12 to 15 is a leaflet 14′ wherein the straight lines lie in a set of parallel planes at an angle "Z" of about 90 degrees; as a result, the concave and convex surfaces extend from the central ridge 80′ to the outward edge 84′ with a slightly upstream orientation, as can be seen by the sectional views of FIG. 15 which are taken along such a set of 3 parallel planes. Such an orientation slightly accentuates the convex regions 72′ in the inflow surface of each leaflet.

Overall, this type of construction where the concave and convex surfaces regions are formed of such straight lines is referred to as a "twisted ribbon" construction. In other words, it can be thought of as being formed of ribbons which are made up of an infinite number of straight line segments with each of the convex and concave regions retaining its rectilinear configuration, although one edge of the ribbon (i.e. that edge along the midplane) has an undulating orientation and the other edge 84, 84′ is that of a simple curve. For example, in the leaflet 14′ of FIG. 12, the straight line segments of the rectilinear surfaces on each side of the central ridge 80′ lie in planes at an angle "Z" of about 90 degrees to the flat surface 75′ and perpendicular to the midplane, as result of which the composite curved surfaces have a slightly upstream orientation and may provide particularly effective turbulence-alleviating performance.

In such a twisted ribbon orientation, there can be a slight bowing of the straight line segments which make up different portions of the curved surfaces, either upward or downward, without departing from the benefits which flow therefrom, and such are considered to be equivalents. Such twisted ribbon style is repeated on the other half of the leaflet so that the leaflet, as explained hereinbefore, is essentially made up of two integral halves split by the central plane, which halves are mirror images of each other.

Following fabrication of the leaflets and valve body 12, installation is effected by squeezing the valve body at diametrically opposed locations so that it spreads out sufficiently to accommodate the leaflets 14 between the flat surfaces 24, with notches 53 being fitted about the valve body projections 42. As soon as the force squeezing the valve body is removed, it returns to its cylindrical shape, and if desired, a stabilizing ring, as is well known in the art, can be installed, as by shrink-fitting, about the exterior surface of the valve body 12 so as to assure that the valve body will retain its precise circular cross sectional configuration. As best seen in FIG. 2, in the installed position, the flat upstream sections of the leaflets are disposed between the abutments 26 and the pivot projections 52, with the notches being located in mating engagement with the pivot projections 42 which allow the leaflets to both rotate and slide somewhat in moving between their open and closed positions.

In FIG. 1, the leaflets are shown with the inflow surfaces 30 lying generally adjacent the relatively flat surfaces of the abutments 26, which surfaces are parallel to the centerline of the valve, and with the outflow surfaces 32 abutting the downstream stop surfaces of the protrusions 27, both of which together define the extent of the opening movement of the leaflets. In the closing movement, the edges 77 of the downstream protrusions 27 engage the oblique surfaces 59 of the extensions just before the leaflets reach this full open position, and as a result of this sliding contact between the edges 77 and these surfaces, the leaflets are lifted slightly in an upstream direction to break contact between the interengaging surfaces of the notches and the pivots 43 just before the leaflets complete their opening movement.

In the open position, the leaflets 14 are preferably positioned with the flat sections 57, that lie just upstream of the curved sections 58, oriented parallel to the centerline of the valve passageway; the leaflets thus present minimum obstruction to blood flow therethrough. As best seen in FIG. 2, the downstream portions of the leaflets curve away from the centerline of the valve, and this orientation assures a quick response to reverse flow so that the leaflets 14 close very promptly with a minimum amount of regurgitation. The angle of opening of the leaflets is identified by the reference letter "a" (FIG. 2) which preferably has a value between about 70 degrees and about 87 degrees. More preferably the angle of opening is not greater than about 85 degrees, and most preferably the angle is between about 77 degrees and about 83 degrees. The angle a is defined by a pair of planes L and M depicted in FIG. 2. Both planes are perpendicular to the flat surfaces 24 of the valve body 12, with the plane L containing the centerline of the valve. The plane M passes through the midsection of the mating surface 38 of the leaflet and also bisects the downstream section of the arcuate peripheral surface 36. The streamlined curvature of the inflow surfaces and outflow surfaces of the leaflets assures that there is minimal boundary layer separation where the bloodstream contacts the angularly oriented leaflet surfaces.

When the reversal of blood flow occurs so that backflow of the blood is in the opposite direction to the arrows 18 in FIG. 2, the backflowing blood applies force against the outflow surfaces 32, one vector of which force causes pivoting to immediately begin. During the initial closing movement of the leaflets, the leaflets are displaced slightly upstream by another vector of the force, and there is engagement between the pivots 43 and the curved surface 58 of the notches 53 which further promotes pivoting. At the same time, the downstream edge of the abutment 26 serves as a fulcrum about which the closing pivoting occurs. The magnitude of this force vector causing pivoting continues to increase as the leaflets become more transverse to the direction of flow until closing occurs, as illustrated in FIG. 4, with the arcuate peripheral surfaces 36 in contact with the interior right circular cylindrical surface 20 of the valve body 12. The leaflets come to rest in the closed position with flat section 68 of each inflow surface in juxtaposition to the corresponding oblique surface on the abutment 26, and with the mating surfaces 38 of the two leaflets in juxtaposition to each other and preferably abutting each other.

Overall, the heart valve 10 constructed as illustrated in the drawings has advantageous features not found in earlier heart valves because it combines low pressure drop and freedom from thrombosis and hemolysis with quick instigation of opening and closing movement. As a result of the three-dimensional curvature of the inflow surface, the velocity of the bloodstream layer flowing along a major portion of the inflow surface more closely approaches the velocity of the bloodstream layer flowing along the outflow surface, thereby reducing turbulence where these layers merge. Although the illustrated embodiments constitute the best mode presently known to the inventors, it should be understood that various changes and modifications which would be obvious to one having the ordinary skill in this art may be made without departing from the scope of the invention which is defined by the claims appended hereto. For example, although the heart valve components are preferably made from pyrocarbon-coated substrates or from total pyrocarbon, the improved flow characteristics will also be a feature of heart valves made from other comparable construction materials that are likewise durable and nonthrombogenic. Particular features of the invention are set forth in the claims appended hereto.

WHAT IS CLAIMED IS:

1. A prosthetic heart valve comprising
   an annular valve body having an internal surface that defines an interior passageway for the flow of blood therethrough, the exterior of which body facilitates attachment of a device to mount the prosthetic valve in a mammalian heart,
   occluder means for permitting the flow of blood in a downstream direction through said passageway while preventing substantial backflow of blood in an upstream direction,
   pivot means mounting said occluder means within said interior passageway of said valve body so as to pivot to and from positions allowing blood flow in a downstream direction and blocking blood flow in an upstream direction,
   said occluder means having inflow and outflow major surfaces which face in opposite directions, the edges of which major surfaces terminate at a peripheral surface which resides generally adjacent said valve body internal surface when said occluder means is in the blocking position, said inflow major surface facing upstream and said outflow major surface facing downstream in said blocking position,
   said outflow surface having a generally flat portion located in the region of said pivot means and having a convex portion in a region downstream of said flat portion,
   said inflow surface having a concave region which is joined smoothly to a convex region located downstream thereof,
   said peripheral surface in the region contiguous to said inflow concave and convex surface regions being of substantially constant thickness while said occluder means varies significantly in thickness in the vicinities of said concave and convex surface regions, and
   said convex inflow surface region being defined by curved surfaces that extend smoothly in generally laterally opposite directions from a central ridge to said peripheral surface, said central ridge being located along a central plane that bisects said occluder means.

2. A heart valve according to claim 1 wherein the cross section of said interior passageway is generally circular and wherein said occluder means includes a pair of leaflets of substantially identical design which are mounted to a pivot about a pair of parallel axes within said valve body.

3. A heart valve according to claim 2 wherein said peripheral surface of each of said leaflets includes a flat surface section which lies parallel to said pivot axis, said flat surface sections of said two leaflets abutting each other when said occluder means is in the blocking position.

4. A heart valve according to claim 3 wherein said central ridge of each leaflet lies along a central plane which is perpendicular to said pivot axis and bisects the length of said leaflet pivot axis, and said convex surface region is tangent to said concave surface region at a point along said central ridge.

5. A heart valve according to claim 4 wherein said interior passageway is circular and wherein, when said leaflets are in the blocking position, said point of tangency in said central plane is located a radial distance from the centerline of said valve interior passageway equal to between about 0.6 R and about 0.7 R, with R being the radius of said circular interior passageway.

6. A heart valve according to claim 4 wherein said interior passageway is circular and wherein said convex surface region has a radius of curvature measured in said central plane of between about 0.5 R and about 0.7 R, with R being the radius of said circular interior passageway.

7. A heart valve according to claim 4 wherein said inflow and outflow surfaces have generally coextensive planar portions which define an upstream section of each of said leaflets, said planar portions being parallel and spaced apart at a distance t.

8. A heart valve according to claim 7 wherein said thickness of each leaflet increases in the downstream direction from said upstream planar section to a maximum thickness of about 2t measured along said central plane.

9. A heart valve according to claim 7 wherein said convex and concave regions of each said leaflet when cut by a series of planes oriented parallel to said central plane have radii of curvature that increase substantially uniformly in length outward from said central plane is a direction generally perpendicular to said central plane.

10. A heart valve according to claim 9 wherein said increase in curvature is proportioned such that the intersection of said curved surface regions with the leaflet peripheral surface results in a leaflet edge that is substantially equidistant from the similar edge of said outflow surface and wherein the thickness of said surface in said contiguous region is equal to about t.

11. A prosthetic heart valve according to claim 5 wherein said inflow surface of each said leaflet has two halves lying on opposite sides of said central plane, which are mirror images of each other.

12. A heart valve according to claim 1 wherein the radius of curvature of said convex inflow surface, as measured in a series of planes parallel to said central plane, increases in a direction laterally outward from said central plane.

13. A prosthetic heart valve comprising an annular valve body having an internal surface that defines an interior passageway for the flow of blood therethrough,
    occluder means for permitting the flow of blood in a downstream direction through said passageway while preventing substantial backflow of blood in an upstream direction,
    pivot means mounting said occluder means within said interior passageway of said valve body so as to pivot to and from positions allowing blood flow in a downstream direction and blocking blood flow in an upstream direction,
    said occluder means having inflow and outflow major surfaces which face in opposite directions, the edges of which major surfaces terminate at a peripheral surface which resides generally adjacent said valve body internal surface when said occluder means is in the blocking position, said inflow major surface facing upstream and said outflow major surface facing downstream in said blocking position,
    said outflow surface having a generally flat portion located in the region of said pivot means and having a convex portion in a region downstream of said flat portion,
    said inflow surface having a concave region which is joined smoothly to a convex region located downstream thereof, and
    said convex inflow surface region extends from a central ridge that bisects said occluder means to said peripheral surface and is defined by a plurality of substantially straight lines which lie in planes perpendicular to said central plane, which straight lines slope downward from said central ridge.

14. A heart valve according to claim 13 wherein said occluder means includes a pair of leaflets of substantially identical design which are mounted to a pivot about a pair of parallel axes within said valve body and wherein, in each leaflet, said peripheral surface in the region contiguous to said inflow concave and convex surface regions is defined by an arcuate inflow edge and a similarly arcuate outflow edge and is of substantially constant thickness.

15. A prosthetic heart valve according to claim 14 wherein each of said plurality of straight lines forms an angle of between about 95° and about 110° with the line which said perpendicular plane cuts in said peripheral surface.

16. A heart valve according to claim 13 wherein said annular valve body has a circular passageway therethrough and wherein said inflow surface includes a planar region which extends from a location upstream of said pivot axis to a location downstream therefrom, which planar region is substantially parallel to said flat portion of said outflow surface.

17. A prosthetic heart valve according to claim 13 wherein said arcuate portion of said peripheral surface is of substantially uniform thickness along its entire length and said inflow convex surface extends from said curved peripheral surface at an angle of between about 24° and about 27°, said angle being measured in said central plane between a line which is tangent to said inflow convex surface and a line which is perpendicular to the centerline of said interior passageway with said leaflet in the blocking position.

18. A heart valve according to claim 13 wherein the radius of curvature of said convex inflow surface, as measured in a series of planes parallel to said central plane, increases in a direction laterally outward from said central plane.

19. A heart valve according to claim 13 wherein the radius of curvature of said concave inflow surface, as measured in a series of planes parallel to said central plane, increases in a direction laterally outward from said central plane.

20. A prosthetic heart valve comprising an annular valve body having an internal surface that defines an interior passageway for the flow of blood therethrough, a pair of substantially identical occluders for permitting the flow of blood in a downstream direction through said passageway while preventing substantial backflow of blood in an upstream direction, pivot means mounting said occluders within said interior passageway of said valve body so as to pivot to and from positions allowing blood flow in a downstream direction and blocking blood flow in an upstream direction, each said occluder having inflow and outflow major surfaces which face in opposite directions, the edges of which major surfaces terminate at a peripheral surface which resides generally adjacent said valve body internal surface when said occluders are in the blocking position, said inflow major surface facing upstream and said outflow major surface facing downstream in said blocking position, both said major surfaces having a generally flat portion located in the region of said pivot means which flat portions are substantially parallel to each other, said outflow surface having a convex portion in a region downstream of said flat portion, said inflow surface having a concave region downstream of said flat portion which region is joined smoothly to a convex region located downstream thereof, said convex and concave inflow surface regions extending from a central ridge that bisects said occluder means to said peripheral surface and being defined by a plurality of substantially straight lines which lie in planes perpendicular to said central plane, which straight lines slope downward from said central ridge.

* * * * *

UNITED STATES PATENT AND TRADEMARK OFFICE
CERTIFICATE OF CORRECTION

PATENT NO. : 5,108,425
DATED : April 28, 1992
INVENTOR(S) : Hwang, Ned H.C.

It is certified that error appears in the above-identified patent and that said Letters Patent is hereby corrected as shown below:

<u>IN THE CLAIMS</u>: Claim 9, column 11, line 39, "is" should be --in--. Claim 11, column 11, line 48, "5" should be --4--.

Signed and Sealed this

Third Day of August, 1993

Attest:

MICHAEL K. KIRK

*Attesting Officer*    *Acting Commissioner of Patents and Trademarks*